(12) United States Patent
Liu et al.

(10) Patent No.: US 10,631,824 B2
(45) Date of Patent: Apr. 28, 2020

(54) MEDICAL BODY SURFACE STICKING ULTRASONIC PROBE

(71) Applicant: SHENZHEN MINDRAY BIO-MEDICAL ELECTRONICS CO., LTD., Shenzhen (CN)

(72) Inventors: Shuo Liu, Shenzhen (CN); Yong Li, Shenzhen (CN); Jianhui Liu, Shenzhen (CN); Qun Lin, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 279 days.

(21) Appl. No.: 15/195,590

(22) Filed: Jun. 28, 2016

(65) Prior Publication Data

US 2016/0302765 A1    Oct. 20, 2016

Related U.S. Application Data

(63) Continuation of application No. PCT/CN2014/077329, filed on May 13, 2014.

(30) Foreign Application Priority Data

Dec. 30, 2013 (CN) .......................... 2013 1 0738358

(51) Int. Cl.
*A61B 8/00* (2006.01)

(52) U.S. Cl.
CPC .......... *A61B 8/4236* (2013.01); *A61B 8/4281* (2013.01); *A61B 8/4455* (2013.01)

(58) Field of Classification Search
CPC ....... A61B 8/44; A61B 8/4236; A61B 8/4272; A61B 8/4281; A61B 8/4455;
(Continued)

(56) References Cited

U.S. PATENT DOCUMENTS 3,299,882 A * 1/1967 Masino .................. A61B 5/021
                                                        600/398
4,111,464 A * 9/1978 Asano ..................... F16L 47/12
                                                        285/111
(Continued)

FOREIGN PATENT DOCUMENTS

CN    102824191 A    12/2012
CN    202568309 U    12/2012
(Continued)

OTHER PUBLICATIONS

Zuo; Yunxia., Sticking type medical in-vitro ultrasonic probe, Dec. 2012, CN102824191A, machine translated english.*

(Continued)

*Primary Examiner* — Oommen Jacob
(74) *Attorney, Agent, or Firm* — Kory D. Christensen

(57) ABSTRACT

A medical body surface ultrasonic probe may comprise a probe body and a sticking plate, where the sticking plate may comprise a sub-plate. The sub-plate may be connected to the probe body, and the bottom of the sub-plate may have a sticking layer for attaching a medical body surface ultrasonic probe to a body surface of a monitored user. The medical body surface ultrasonic probe can be used where prolonged, continuous ultrasonic monitoring is required. In addition, a corresponding ultrasonic diagnostic apparatus is also provided.

14 Claims, 3 Drawing Sheets

(58) Field of Classification Search
CPC ...... A61B 2017/3492; A61B 2050/002; A61B 2017/06033; A61B 5/04087; A61B 5/6833; A61B 5/6832; A61B 2046/205; A61B 17/3423; A61B 17/3462; A61B 2017/0065; A61B 2017/3425; A61B 8/00; G01S 7/52079; A61F 13/148; A61F 13/02; A61M 25/02; A61M 2025/0266; A61M 2025/0246; Y10S 285/921

USPC .......................................... 600/459, 4.7, 437

See application file for complete search history.

(56) References Cited

U.S. PATENT DOCUMENTS

| | | | | |
|---|---|---|---|---|
| 4,920,966 | A * | 5/1990 | Hon | A61B 5/4356 600/459 |
| 4,947,853 | A * | 8/1990 | Hon | A61B 5/022 600/459 |
| 5,058,592 | A * | 10/1991 | Whisler | A61B 8/4281 128/DIG. 15 |
| 5,070,888 | A * | 12/1991 | Hon | A61B 5/02233 600/588 |
| 5,168,876 | A * | 12/1992 | Quedens | A61B 5/0416 600/376 |
| 5,381,794 | A * | 1/1995 | Tei | A61B 8/4209 600/459 |
| 5,390,675 | A * | 2/1995 | Sheehan | A61B 8/4209 600/453 |
| 5,394,877 | A * | 3/1995 | Orr | A61B 5/0408 600/459 |
| 6,048,323 | A * | 4/2000 | Hon | A61B 5/4356 600/588 |
| 6,117,086 | A * | 9/2000 | Shulze | A61B 5/0215 600/486 |
| 6,261,231 | B1 * | 7/2001 | Damphousse | A61B 8/4209 600/437 |
| D674,099 | S * | 1/2013 | Nichols | D24/189 |
| 8,525,643 | B2 * | 9/2013 | Green | A61B 5/0002 340/5.8 |
| 8,687,299 | B1 * | 4/2014 | Sanford | F16B 21/04 359/827 |
| 8,876,720 | B2 * | 11/2014 | Vezina | A61B 5/02028 600/459 |
| D787,687 | S * | 5/2017 | Vezina | D24/187 |
| 9,743,907 | B2 * | 8/2017 | Mailaender | A61B 8/0866 |
| 10,226,207 | B2 * | 3/2019 | Stafford | A61B 5/6832 |
| 2003/0135241 | A1 * | 7/2003 | Leonard | A61N 1/05 607/2 |
| 2004/0024348 | A1 * | 2/2004 | Redding, Jr. | A61K 9/0009 604/22 |
| 2005/0215901 | A1 * | 9/2005 | Anderson | A61B 8/12 600/445 |
| 2006/0015059 | A1 * | 1/2006 | Redding, Jr. | A61K 9/0009 604/22 |
| 2007/0167817 | A1 * | 7/2007 | Huang | A61B 8/0833 600/461 |
| 2008/0241199 | A1 * | 10/2008 | Silverman | A61B 5/0261 424/400 |
| 2008/0306388 | A1 * | 12/2008 | Tanis | A61N 7/00 600/459 |
| 2009/0177083 | A1 * | 7/2009 | Matsumura | A61B 8/08 600/437 |
| 2009/0318813 | A1 * | 12/2009 | Thompson | A61B 17/225 600/459 |
| 2010/0022888 | A1 * | 1/2010 | George | A61B 8/02 600/459 |
| 2012/0046592 | A1 * | 2/2012 | Albright | A61N 7/02 604/2 |
| 2012/0197165 | A1 * | 8/2012 | Tanis | A61N 7/00 601/2 |
| 2015/0065856 | A1 * | 3/2015 | Tretbar | A61B 8/4209 600/411 |
| 2015/0127041 | A1 * | 5/2015 | Clark, III | A61B 17/32002 606/171 |
| 2015/0290477 | A1 * | 10/2015 | Jahnke | A61N 7/00 601/2 |
| 2016/0106390 | A1 * | 4/2016 | Vezina | A61B 5/6833 600/459 |
| 2016/0302765 | A1 * | 10/2016 | Liu | A61B 8/4236 |

FOREIGN PATENT DOCUMENTS

| | | | |
|---|---|---|---|
| CN | 202776369 U | * | 3/2013 |
| JP | H05305082 A | | 11/1993 |
| JP | 2006230912 A | | 9/2006 |
| WO | 9712552 | | 4/1997 |

OTHER PUBLICATIONS

Wei; He, "Ultrasonic probe connecting device applied to intracranial pressure detection", CN202568309, Dec. 2012, machine translated English (Year: 2012).*

Zuo; Yunxia, "Sticking type medical in-vitro ultrasonic probe", CN202776369, Mar. 2013, machine translated English (Year: 2013).*

Bayer Material Science, "Snap-fit joints for plastics: A design guide," Pittsburgh, Pennsylvania, USA: 2013 (Year: 2013).*

* cited by examiner

MEDICAL BODY SURFACE STICKING ULTRASONIC PROBE

FIELD

The present disclosure relates to the field of medical devices, particularly to a medical body surface ultrasonic probe and an ultrasonic diagnostic apparatus.

BACKGROUND

An ultrasonic diagnostic apparatus is an instrument for generating an incident ultrasonic wave (transmitting wave) through an ultrasonic probe to enter human tissue, receiving reflected ultrasonic waves (echoes) of interfaces of the human tissue and then processing these reflected signals so as to obtain a human tissue image. The ultrasonic probe, an important component of the ultrasonic diagnostic apparatus, has a strong effect on detection. Different ultrasonic probes are used for different imaging regions. The probes also have different sizes, shapes and operating frequencies for different ages, figures and positions of scanned tissue and organs of patients.

The existing medical ultrasonic probe generally has a non-fixed structure, and is handheld by a doctor during use and is pressed on a detected position of a detected person. The ultrasonic probe is rotated, moved or pressurized according to imaging needs to obtain an ultrasonic image. However, the ultrasonic probe is secured to a certain position of the human body for a long time during examination of some diseases. The ultrasonic probe with the non-fixed structure has difficulty adapting to it due to an increase of labor intensity and waste of human power caused by the ultrasonic probe, and is secured to a certain position of the human body for a long time by the doctor's hands as well as an influence on a detection effect caused by inevitable change of a handhold position.

"An ultrasonic probe with an absorbing adjusting device" is disclosed in Chinese Patent No. CN200820063012.9. The ultrasonic probe is connected with an absorbing device, and is secured to the surface of a human body through the absorbing device during use. The absorbing device secures the ultrasonic probe via negative pressure. However, the surface of the human body is not flat and smooth, and the absorbing device may leak and become loose due to slight collision or disturbance, resulting in an influence on the securing stability of the ultrasonic probe.

BRIEF SUMMARY

To at least partly eliminate the above drawback in the prior art, the present disclosure proposes a medical body surface ultrasonic probe and an ultrasonic diagnostic apparatus which can ensure that the probe is stably attached to the body surface of a human body for a long time for use in a clinical situation where a prolonged continuous ultrasonic monitoring is required.

To at least partly solve the above technical problem, embodiments of the present disclosure provide a medical body surface ultrasonic probe which may comprise a probe body and a sticking plate, wherein the sticking plate may comprise a sub-plate. The sub-plate may be connected with the probe body, and the bottom of the sub-plate may be provided with a sticking layer used for sticking or attaching the medical body surface ultrasonic probe to a body surface of a monitored user.

In some embodiments, the sticking plate may comprise a plurality of independent sub-plates. A clamping piece may be arranged at one end part of each of the sub-plates. Each of the clamping pieces may be matched with a corresponding clamping groove arranged outside of the probe body. The plurality of sub-plates may be arranged in a fan shape.

In some embodiments, the sticking plate and the probe body may be formed integrally.

In some embodiments, the sticking plate may further comprise a connecting body which may connect the probe body and the sticking plate, and the connecting body may be of a tubular structure and may comprise a sleeve which may be sleeved outside of the probe body, and a plurality of clamping grooves which may be arranged on an inner wall of the sleeve and connected to the sticking plate.

In some embodiments, the sticking plate may further comprise an annular ring through which the probe body may pass. A plurality of sub-plates may extend outwards from the periphery of the annular ring. A plurality of clamping pieces may be arranged on the annular ring, and may be matched with the plurality of clamping grooves on the connecting body.

In some embodiments, the sticking plate may comprise a plurality of independent sub-plates. A clamping piece may be arranged at one end part of each of the sub-plates, and each of the clamping pieces may be matched with a corresponding clamping groove on the connecting body. The plurality of sub-plates may be arranged in a fan shape.

In some embodiments, the section of each sub-plate may have an arc shape, and one side of the sub-plate used for sticking on a monitored user may be curved towards the body surface of the monitored user.

In some embodiments, the sticking layer may be a double-sided adhesive tape.

Accordingly, embodiments of the present disclosure also provide a medical body surface ultrasonic probe which may comprise a probe body and a sticking plate. The sticking plate may comprise at least two sticking regions, and a gap for at least partially separating the at least two sticking regions may be provided between adjacent sticking regions. A sticking layer may be arranged on each sticking region for sticking or attaching the medical body surface ultrasonic probe to the body surface of the monitored user.

In some embodiments, the gap may be a bar-shaped gap.

In some embodiments, the sticking plate may be provided with a plurality of clamping pieces, and each of the clamping pieces may be matched with a corresponding clamping groove arranged at the probe body.

In some embodiments, the sticking plate and the probe body may be formed integrally.

In some embodiments, the sticking plate may further comprise a connecting body used for connecting the probe body and the sticking plate. The connecting body may be of a tubular structure and may comprise a sleeve for sleeving the probe body, and a plurality of clamping grooves which may be arranged on an inner wall of the sleeve and used for connecting the sticking plate.

In some embodiments, the sticking plate may be provided with a plurality of clamping pieces which may be matched with a plurality of clamping grooves on the connecting body.

In some embodiments, the section of the sticking plate on the at least two sticking regions may have an arc shape, and one side of the sticking plate used for sticking onto a monitored user may be curved towards the body surface of the monitored user.

In some embodiments, the sticking layer may be a double-sided adhesive tape.

Embodiments of the present disclosure also provide a medical body surface ultrasonic probe which may comprise a probe body and at least two sticking plates used for fixing the probe onto the human body. The at least two sticking plates may be substantially located in the same plane, and a gap may be provided between adjacent sticking plates.

The bottom of each of the sticking plates may be provided with a sticking layer used for sticking or attaching the medical body surface ultrasonic probe to the body surface of the monitored user.

In some embodiments, a clamping piece may be arranged on one end part of each of the sticking plates, and each of the clamping pieces may be matched with a corresponding clamping groove arranged on the probe body.

In some embodiments, the sticking plate and the probe body may be formed integrally.

In some embodiments, the sticking plate may further comprise a connecting body used for connecting the probe body and the sticking plate. The connecting body may be of a tubular structure and may comprise a sleeve for sleeving the probe body and a plurality of clamping grooves which may be arranged on an inner wall of the sleeve and used for connecting the sticking plate.

In some embodiments, a clamping piece may be arranged on one end part of each of the sticking plates, and each of the clamping pieces may be matched with a plurality of clamping grooves on the connecting body.

In some embodiments, the section of each sticking plate may have an arc shape, and one side of the sticking plate used for attaching the probe to a monitored user may be curved towards the body surface of the monitored user.

In some embodiments, the sticking layer may be a double-sided adhesive tape. Embodiments of the present disclosure also provide an ultrasonic diagnostic apparatus which may at least comprise the aforementioned ultrasonic probe.

The embodiments of the present disclosure may have some advantages.

The medical body surface ultrasonic probe of the embodiments of the present disclosure may comprise a sticking plate. A sticking layer may be arranged on the sticking plate. Therefore, the ultrasonic probe can be secured to the body surface of a user to be monitored in a sticking manner, and thus the requirements of an occasion where the ultrasonic probe is required to be stably attached to the surface of a human body for a long time can be satisfied.

Meanwhile, the sticking plate can be designed to comprise a plurality of independent sub-plates, and each sub-plate may be individually connected with the connecting body. Therefore, if one of the sub-plates comes loose, other sub-plates will not be affected, thereby ensuring proper operation of the ultrasonic probe.

In addition, the sub-plates may be arranged in an arc shape. One side of the sub-plate used for sticking the probe on a monitored user may be curved towards the body surface of the monitored user, and thereby a tight attachment of the ultrasonic probe on the human body can be obtained, the attaching time of the ultrasonic probe onto the human body can be achieved, and the requirement for a prolonged continuous ultrasonic monitoring can be better satisfied.

BRIEF DESCRIPTION OF THE DRAWINGS

To more clearly describe the technical solutions in the embodiments of the present disclosure or in prior art, the drawings referenced by the description of the embodiments of the present disclosure or by the prior art are presented below. The drawings accompanying this application show a few of the embodiments of the present disclosure, and for those skilled in the art, other drawings can also be obtained according to these drawings without contributing creative labor.

DETAILED DESCRIPTION

The technical solutions in the embodiments of the present disclosure are more fully described below, along with the drawings in the embodiments of the present disclosure. The described embodiments are merely a few of the embodiments of the present disclosure. Based on the embodiments in the present disclosure, all other embodiments obtained by those skilled in the art without contributing creative labor are part of the protection scope of the present disclosure.

Figure 1:
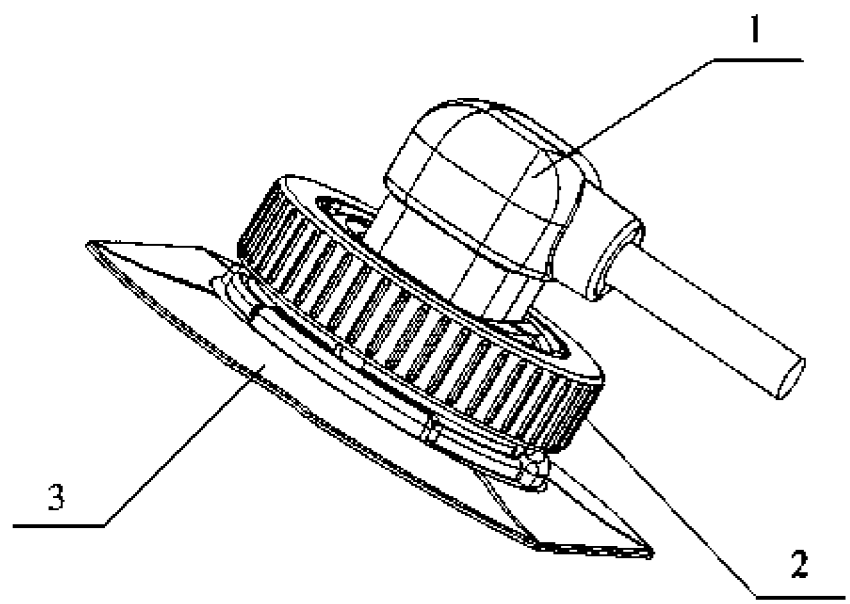
FIG. 1 is a structural diagram of one embodiment of an anti-loosening, sticking type medical body surface ultrasonic probe of the present disclosure.
Figure 2:
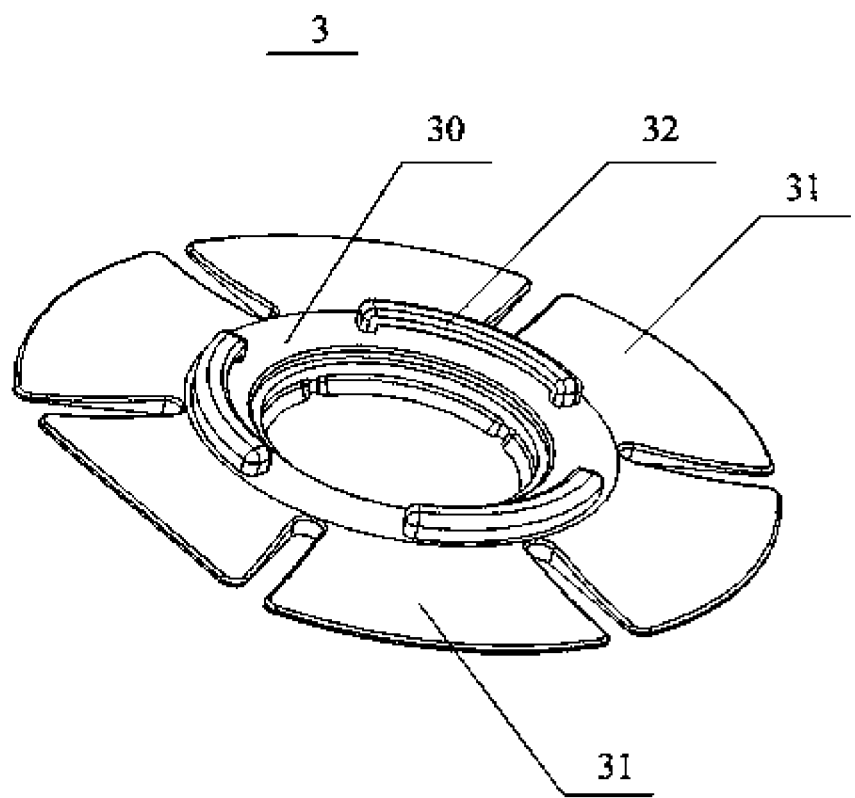
FIG. 2 is a structural diagram of a sticking plate in FIG. 1.

As shown in FIG. 1 and FIG. 2, a structural diagram of one embodiment of a medical body surface ultrasonic probe of the present disclosure is shown. In the embodiment, the ultrasonic probe may comprise a probe body 1, a connecting body 2 and a sticking plate 3.

The connecting body 2 may connect the probe body 1 and the sticking plate 3, and a window may be arranged in the middle position of the connecting body 2 for exposing a transducer (not shown) of the probe body 1.

The sticking plate 3 may comprise at least one sub-plate 31. One end of the at least one sub-plate 31 may be connected to the connecting body 2, and the bottom of the at least one sub-plate 31 may be provided with a sticking layer for sticking or attaching a body surface ultrasonic probe to a body surface of a monitored user.

Specifically, the connecting body 2 may be of a tubular structure and may comprise a sleeve for sleeving the probe body and a plurality of clamping grooves which may be arranged on an inner wall of the sleeve and used for connecting the sticking plate 3.

The sticking plate 3 may further comprise an annular ring 30 through which the probe body 1 may pass. One end of a plurality of sub-plates 31 may be connected to the periphery of the annular ring 30, and the other part of each of the sub-plates 31 may extend outwards. A plurality of clamping pieces 32 may be arranged on the annular ring 30 and may be matched with the plurality of clamping grooves on the connecting body 2 so as to secure the sticking plate 3 to the connecting body 2.

Viscose may be arranged on the sticking layer on the sticking plate 3. For example, a hydrogel layer may be applied using double-sided adhesive tape. The sticking layer may be attached to the sticking plate 3 before use and discarded after use. It should be understood that the viscose on the sticking layer may have sufficient stickiness for ensuring that the ultrasonic probe can be attached to the body surface of the monitored user for a long time (e.g., more than 8 hours).

Figure 3:
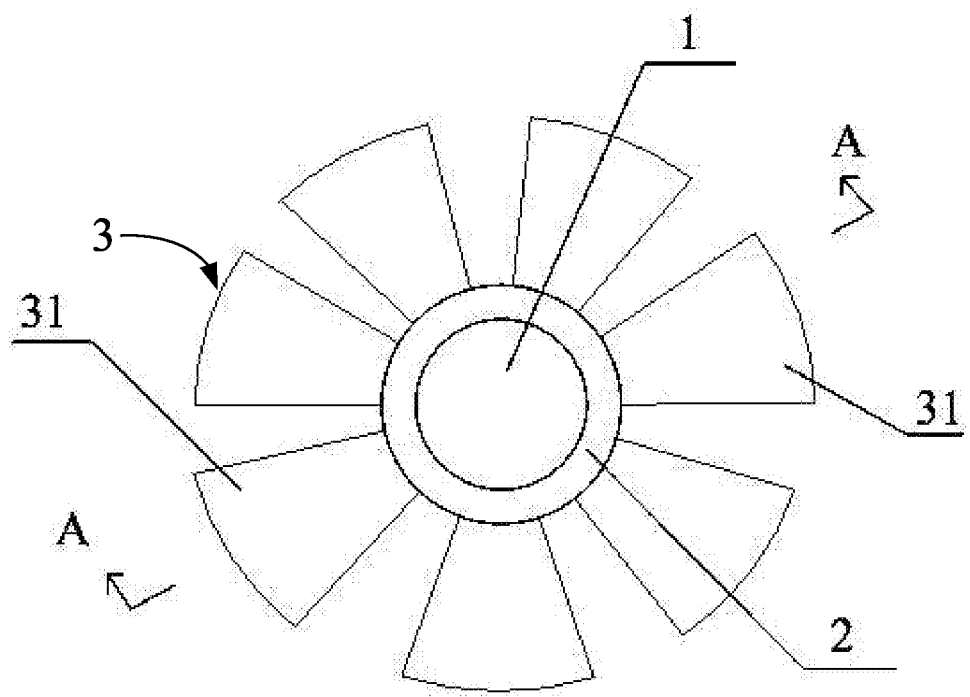
FIG. 3 is a top view of another embodiment of a medical body surface ultrasonic probe of the present disclosure.
Figure 4:
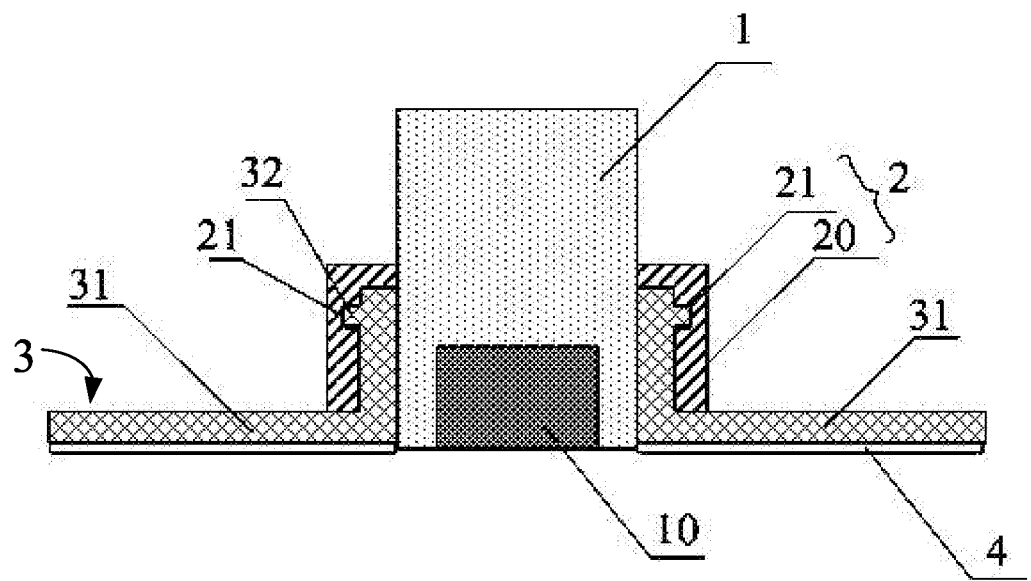
FIG. 4 is an A-A directional section view of FIG. 3.

As shown in FIG. 3 and FIG. 4, a structural diagram of another embodiment of a medical body surface ultrasonic probe of the present disclosure is shown. In the embodiment, the ultrasonic probe may comprise a probe body 1, a connecting body 2 and a sticking plate 3.

The connecting body 2 may be used for connecting the probe body 1 and the sticking plate 3, and a window may be arranged in the middle position of the connecting body 2 for exposing a transducer 10 of the probe body 1.

Specifically, the connecting body 2 may be of a tubular structure and may comprise a sleeve 20 for sleeving the probe body and a plurality of clamping grooves 21 which may be arranged on the inner wall of the sleeve 20 and used for connecting the connecting body 2.

The sticking plate 3 may comprise a plurality of independent sub-plates 31. A clamping piece 32 may be arranged on one end part of each sub-plate 31, and each clamping piece 32 may be directly matched with a corresponding clamping groove 21 on the connecting body 2. The plurality of sub-plates 31 may be arranged in a fan shape.

Moreover, the bottom of at least one sub-plate 31 may be provided with a sticking layer 4 used for sticking or attaching the body surface ultrasonic probe to a body surface of a monitored user. Viscose may be arranged on the sticking layer 4. For example, a hydrogel layer may be applied using double-sided adhesive tape. The sticking layer 4 may be attached to the sticking plate 3 before use, and discarded after use. It should be understood that the viscose on the sticking layer 4 may have sufficient stickiness for ensuring that the ultrasonic probe can be attached to the body surface of the monitored user for a long time.

In the embodiment, because the sticking plate 3 may be designed to comprise a plurality of independent sub-plates 31 and each sub-plate may be individually connected with the connecting body 2, when one of the sub-plates 31 comes loose, other sub-plates 31 may not be affected, thereby ensuring proper operation of the ultrasonic probe.

Figure 5:
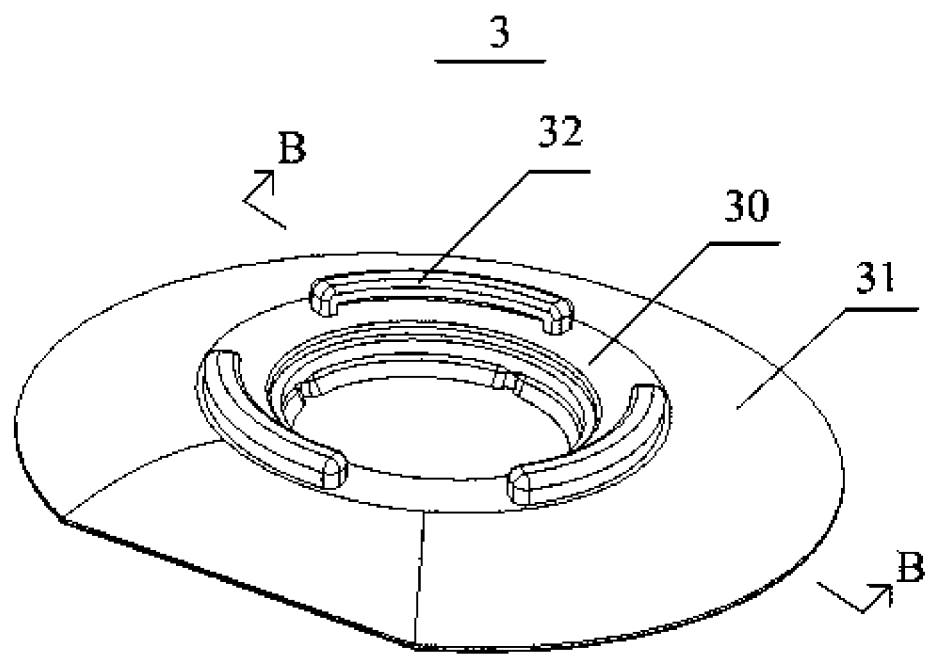
FIG. 5 is a structural diagram of another embodiment of a medical body surface ultrasonic probe of the present disclosure.
Figure 6:
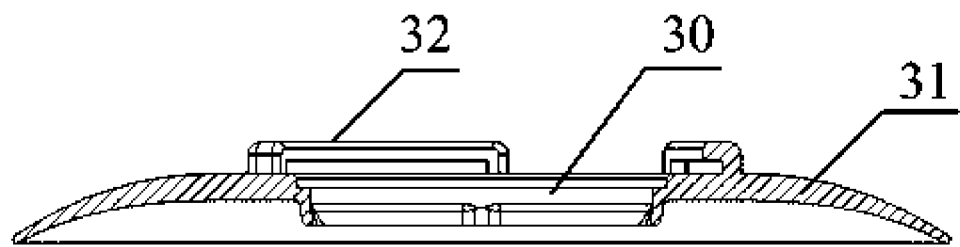
FIG. 6 is a B-B directional section view of FIG. 5.

In FIG. 5 and FIG. 6, a structural diagram of a sticking plate 3 in another embodiment of a medical body surface ultrasonic probe of the present disclosure is shown. In the embodiment, the sticking plate 3 may comprise at least one sub-plate 31. One end of the at least one sub-plate 31 may be connected to the connecting body 2, and the bottom of the at least one sub-plate 31 may be provided with a sticking layer 4. The section of each sub-plate 31 of the sticking plate 3 may have an arc shape, and one side of the sub-plate 31 used for attaching the probe to a monitored user may be curved towards the body surface of the monitored user.

It can be understood that in the embodiments shown in FIG. 3 and FIG. 4, a plurality of sub-plates 31 can also be arranged in an arc shape, and one side of the sub-plate 31 used for attaching the probe to a monitored user may be curved towards the body surface of the monitored user.

In the embodiment, the sub-plates 31 may be arranged in an arc shape, forming a tight attachment of the ultrasonic probe to the human body and prolonging the attaching time of the ultrasonic probe to the human body, where prolonged, continuous ultrasonic monitoring is required.

It can be understood that the present disclosure may have many deformations.

In some embodiments, the sticking plate may be directly connected with the probe body. Specifically, in one embodiment, a plurality of clamping grooves may be arranged at the probe body while the sticking plate may comprise a plurality of independent sub-plates, and a clamping piece may be arranged at one end part of each sub-plate. Each clamping piece may be directly matched with a corresponding clamping groove arranged at the probe body. The plurality of sub-plates may be arranged in a fan shape, so that the sticking plate can be fixedly connected to the probe body.

In another embodiment, the sticking plate and the probe body can be formed integrally.

In yet another embodiment, the medical body surface ultrasonic probe may comprise a probe body and a sticking plate. The sticking plate may comprise at least two sticking regions. A gap for at least partially separating the sticking regions may be provided between adjacent sticking regions. The gap may be a bar-shaped gap. A sticking layer may be arranged on each sticking region for sticking or attaching the body surface ultrasonic probe to the body surface of the monitored user.

The probe body may be connected with the sticking plate as follows. For example, the sticking plate may have a plurality of clamping pieces, and each of the clamping pieces may be directly matched with a corresponding clamping groove arranged at the probe body. Or, the sticking plate and the probe body may be formed integrally. Or, a connecting body may be further adopted for connecting the probe body and the sticking plate.

The connecting body may be of a tubular structure and may comprise a sleeve for sleeving the probe body and may have a plurality of clamping grooves which may be arranged on the inner wall of the sleeve and used for connecting the sticking plate. The sticking plate may be provided with a plurality of clamping pieces which may be matched with a plurality of clamping grooves on the connecting body.

The section of the sticking plate on the sticking region may have an arc shape, and one side of the sticking plate used for attaching the probe to a monitored user may be curved towards the body surface of the monitored user. The sticking layer may be made of double-sided adhesive tape, and hydrogel may be applied to each side of the sticking layer.

In still another embodiment, the medical body surface ultrasonic probe may comprise a probe body and at least one sticking plate used for affixing the probe body to the monitored user. If a plurality of sticking plates is provided, a gap may be provided between adjacent sticking plates.

The bottom of each sticking plate may be provided with a sticking layer used for sticking or attaching the body surface ultrasonic probe to a body surface of a monitored user.

The probe body may be connected with the sticking plate as follows. For example, a clamping piece may be arranged on one end part of each sticking plate and each clamping piece may be directly matched with a corresponding clamping groove arranged on the probe body. Or, the sticking plate and the probe body may be formed integrally. Or, a connecting body may connect the probe body and the sticking plate.

The connecting body may be of a tubular structure and may comprise a sleeve for sleeving the probe body and a plurality of clamping grooves which may be arranged on the inner wall of the sleeve and used for connecting the sticking plate. The sticking plate may be provided with a plurality of clamping pieces which may be matched with a plurality of clamping grooves on the connecting body.

The section of each sticking plate may have an arc shape, and one side of the sticking plate used for sticking onto a monitored user may be curved towards the body surface of the monitored user. The sticking layer may be made of double-sided adhesive tape, and hydrogel may be applied to each side of the sticking layer.

Accordingly, the present disclosure also provides an ultrasonic diagnostic apparatus which may at least comprise the aforementioned ultrasonic probe.

The embodiments of the present disclosure may have some advantages.

In some embodiments, the ultrasonic probe of the embodiments of the present disclosure may comprise a sticking plate. A sticking layer may be applied to the sticking plate. The ultrasonic probe can be attached to the body surface of the monitored user. Therefore, the ultrasonic probe can be stably attached to the body surface of a human body for a long time.

Meanwhile, in some embodiments, the sticking plate can be designed to comprise a plurality of independent sub-plates, and each sub-plate may be individually connected with the connecting body. Therefore, if one of the sub-plates comes loose, other sub-plates will not be affected, thus ensuring the proper operation of the ultrasonic probe.

In some embodiments, the sub-plates may be arranged in an arc shape. One side of the sub-plate used for sticking the probe onto a monitored user may be curved towards the body surface of the monitored user, and the probe can provide certain pre-pressure when sticking the probe to the body surface. Therefore, tight attachment of the ultrasonic probe to the human body can be obtained, a long attaching time of the ultrasonic probe to the human body can be achieved, and the requirement for continuous ultrasonic monitoring can be better satisfied.

The "probe body" described in the present disclosure may mean ultrasonic probes of various shapes and sizes. For example, various common probes may have housings for the functional components (such as a transducer, a pad, etc.) or may be "incomplete" ultrasonic probes formed only by core elements (such as a transducer or a piezocrystal, etc.), which are capable of implementing ultrasonic wave transmission and reception.

The sticking layer may be a built-in surface layer of the sticking plate and have sticking substances or small absorbing structures, or may be a sticking substance layer or sticking piece coated by an operator before the probe is used.

The above revealed content covers embodiments of the present disclosure and is not intended to limit the scope of the present disclosure. Therefore, all equivalence modifications made in accordance with the present disclosure shall still be within the scope of the present disclosure.

The invention claimed is:

1. A medical body surface ultrasonic probe, comprising:
a probe body;
a sticking plate, wherein the sticking plate comprises a sub-plate, the sub-plate is connected to the probe body, and a bottom of the sub-plate is provided with a sticking layer configured to stick the medical body surface ultrasonic probe to a body surface of a monitored user; and
a connecting body configured to connect the probe body and the sticking plate, wherein the connecting body comprises a sleeve for sleeving the probe body and a plurality of clamping grooves arranged on an inner wall of the sleeve for connecting with the sticking plate,
wherein the sticking plate is a single plate, and comprises a plurality of independent sub-plates, the plurality of independent sub-plates are a part of the sticking plate, a clamping piece is arranged on one end part of each of the sub-plates, each of the clamping pieces is matched with a corresponding clamping groove arranged on the connecting body, and the plurality of sub-plates are arranged along a circumference direction of the probe body.

2. The medical body surface ultrasonic probe of claim 1, wherein the connecting body is of a tubular structure.

3. The medical body surface ultrasonic probe of claim 2, wherein the sticking plate further comprises an annular ring through which the probe body passes, a plurality of sub-plates extend outwards from a periphery of the annular ring, a plurality of clamping pieces are arranged on the annular ring, and the plurality of clamping pieces are matched with the plurality of clamping grooves on the connecting body.

4. The medical body surface ultrasonic probe of claim 2, wherein the sticking plate comprises a plurality of independent sub-plates, a clamping piece is arranged on one end part of each of the sub-plates, the clamping piece is matched with a corresponding clamping groove on the connecting body, and the plurality of sub-plates are arranged along the circumference direction of the probe body.

5. The medical body surface ultrasonic probe of claim 1, wherein a section of the sub-plate has an arc shape, and one side of the sub-plate configured to attach to a monitored user is curved towards the body surface of the monitored user.

6. The medical body surface ultrasonic probe of claim 5, wherein the sticking layer is a double-sided adhesive tape.

7. A medical body surface ultrasonic probe, the probe comprising:
a probe body,
at least two sticking plates, wherein each of the at least two sticking plates comprises at least one sticking region; at least two gaps are provided for at least partially separating the at least two sticking plates; the at least two sticking plates are arranged along a circumference direction of the probe body, wherein each of the at least two sticking plates comprises a first part which is close to the probe body and a second part which is away from the probe body, and the width of the first part of each of the at least two sticking plates is smaller than the width of the second part of each of the at least two sticking plates; wherein the at least two gaps are arranged along the circumference direction of the probe body;
a connecting body configured to connect the probe body and the at least two sticking plates, wherein the connecting body comprises a sleeve for sleeving the probe body and a plurality of clamping grooves arranged on an inner wall of the sleeve for connecting with the at least two sticking plates; and
a sticking layer arranged on the at least one sticking region for sticking the medical body surface ultrasonic probe to a body surface of a monitored user.

8. The medical body surface ultrasonic probe of claim 7, wherein the at least two sticking plates is provided with a plurality of clamping pieces, and each of the clamping pieces is matched with a corresponding clamping groove on the connecting body.

9. The medical body surface ultrasonic probe of claim 7, wherein the connecting body is of a tubular structure.

10. The medical body surface ultrasonic probe of claim 9, wherein the at least two sticking plates are provided with a plurality of clamping pieces which are matched with a plurality of clamping grooves on the connecting body.

11. The medical body surface ultrasonic probe of claim 7, wherein a section of one or more of the at least two sticking plates in the at least one sticking region has an arc shape, and one side of the at least two sticking plates configured to attach to a monitored user is curved towards the body surface of the monitored user.

12. The medical body surface ultrasonic probe of claim 11, wherein the sticking layer is double-sided adhesive tape.

13. The medical body surface ultrasonic probe of claim 7, wherein the sticking layer is arranged on the bottom of the at least one sticking region.

14. The medical body surface ultrasonic probe of claim 7, wherein each of the at least two sticking plates further comprises at least two sticking regions and at least one gap for partially separating the at least two sticking regions; and the sticking layer on each of the sticking regions are partially separated by the at least one gap for partially separating the at least two sticking regions.

* * * * *